(12) United States Patent
Carlbark et al.

(10) Patent No.: US 7,850,673 B1
(45) Date of Patent: Dec. 14, 2010

(54) WAIST BELT FOR ABSORBENT GARMENTS

(75) Inventors: Olle Carlbark, Kållered (SE); Kenneth Strannemalm, Floda (SE); Ewa Kölby Falk, Gothenburg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/529,638

(22) PCT Filed: Oct. 16, 1998

(86) PCT No.: PCT/SE98/01861
§ 371 (c)(1),
(2), (4) Date: Jun. 5, 2000

(87) PCT Pub. No.: WO99/21522
PCT Pub. Date: May 6, 1999

(30) Foreign Application Priority Data
Oct. 24, 1997 (SE) .................................. 9703882

(51) Int. Cl.
*A61F 13/15* (2006.01)
(52) U.S. Cl. .................. 604/392; 604/387; 604/394
(58) Field of Classification Search .................. 604/386, 604/387, 389, 392–394, 385.03; 2/302, 225
See application file for complete search history.

(56) References Cited

U.S. PATENT DOCUMENTS

| | | | |
|---|---|---|---|
| 3,587,580 A | 6/1971 | Jones, Sr. .................... 128/291 |
| 4,393,865 A | 7/1983 | Lambert | |
| 4,964,860 A | 10/1990 | Gipson et al. | |
| 5,300,055 A | 4/1994 | Buell | |
| H1440 H | 5/1995 | New et al. .................... 604/386 |
| 5,509,914 A | 4/1996 | Osborn, III | |
| 5,607,416 A * | 3/1997 | Yamamoto et al. .......... 604/397 |
| 5,706,524 A * | 1/1998 | Herrin et al. ................... 2/400 |
| 5,904,673 A | 5/1999 | Roe et al. | |
| 6,086,571 A * | 7/2000 | Guevara et al. .......... 604/385.2 |

(Continued)

FOREIGN PATENT DOCUMENTS

EP 0 287 388 A2 10/1988

(Continued)

OTHER PUBLICATIONS

Norwegian Patent Application No. 19954515 -Extract from the files to the Decision of Dec. 4, 1998 in the First Division of the Patent Office.

(Continued)

*Primary Examiner*—Tatyana Zalukaeva
*Assistant Examiner*—Lynne Anderson
(74) *Attorney, Agent, or Firm*—Buchanan Ingersoll & Rooney PC

(57) ABSTRACT

A garment (1) includes an absorbent part (2) and a waist belt (3) which is attached directly or indirectly to the garment (1). The belt (3) includes two belt-portions (7,8) which extend essentially in mutually opposite directions from the absorbent part (2) and which are intended to be fastened together around the wearer of the garment (1). The handling properties and comfort properties of the garment have been greatly improved by using a belt (3) whose stiffness varies in the cross-direction thereof.

30 Claims, 3 Drawing Sheets

U.S. PATENT DOCUMENTS

| | | |
|---|---|---|
| 6,306,121 B1 * | 10/2001 | Damaghi et al. ....... 604/385.03 |
| 6,500,163 B2 | 12/2002 | Rönnberg et al. |
| 6,540,731 B2 | 4/2003 | Magnussson et al. |
| 2001/0034511 A1 | 10/2001 | Hermansson et al. |
| 2002/0091367 A1 | 7/2002 | Kusibojoska et al. |

FOREIGN PATENT DOCUMENTS

| | | |
|---|---|---|
| EP | 0 336 578 A1 | 11/1989 |
| EP | 0 409 307 A2 | 1/1991 |
| EP | 0 418 493 A1 | 3/1991 |
| EP | 0 486 006 A2 | 5/1992 |
| EP | 0 528 282 | 2/1993 |
| EP | 0364 454 B1 | 6/1993 |
| EP | 0 605 012 A1 | 7/1994 |
| EP | 0648 482 A2 | 4/1995 |
| EP | 0 729 329 | 3/1999 |
| EP | 1 216 679 A2 | 6/2002 |
| FR | 2 586 558 | 6/1990 |
| GB | 1 200 177 | 7/1970 |
| GB | 2 216 774 | 10/1989 |
| GB | 2257895 | 1/1993 |
| GB | 2 283 661 A | 5/1995 |
| JP | 9-504976 | 5/1997 |
| TW | 233473 | 11/1994 |
| WO | 91/08725 | 6/1991 |
| WO | 94/26222 | 11/1994 |
| WO | 94/26224 | 11/1994 |
| WO | 94/26225 | 11/1994 |
| WO | 95/13781 | 5/1995 |
| WO | 97/33547 | 9/1997 |
| WO | 97/34037 | 9/1997 |
| WO | 97/38658 | 10/1997 |
| WO | 98/37847 | 9/1998 |
| WO | 99/21522 | 5/1999 |
| WO | 99/37263 | 7/1999 |
| WO | 00/27330 | 5/2000 |
| WO | 01/00129 A1 | 1/2001 |
| WO | 01/74283 A1 | 10/2001 |
| WO | 02/03901 A1 | 1/2002 |
| WO | 02/05739 A1 | 1/2002 |
| WO | 02/22061 A1 | 3/2002 |
| WO | 02/22062 A1 | 3/2002 |
| WO | 02/22063 A1 | 3/2002 |
| WO | 02/22064 A1 | 3/2002 |
| WO | 02/22065 A1 | 3/2002 |
| WO | 02/24134 A1 | 3/2002 |
| WO | 02/24135 A1 | 3/2002 |
| WO | 02/49567 A1 | 6/2002 |
| WO | 02/49568 A1 | 6/2002 |

OTHER PUBLICATIONS

Norwegian Patent Application No. 19954515—Translation of the Second Division of Sep. 27, 2000; Second Division Case No. 6979.
Translation of Notice of Reason of Rejection in JP2000-517685, dated Apr. 6, 2007.

* cited by examiner

WAIST BELT FOR ABSORBENT GARMENTS

FIELD OF INVENTION

The present invention relates to a garment that comprises an absorbent part and a waist belt which is attached directly or indirectly to the garment, wherein the belt has two belt portions that extend in respective opposite directions from said absorbent part and which can be fastened together around the wearer of said garment.

BACKGROUND OF THE INVENTION

Absorbent garments of the aforesaid kind are well known in this field. The garment in question has a belt attached to the absorbent part of the garment and, subsequent to fastening the belt around the wearer's waist with the attached end of the garment located at the rear of the wearer, requires that end of the garment which is not fastened to the belt to be brought between the wearer's thighs and detachably fastened to the front side of the belt with the aid of some type of fastener means. Such releasable fastener means may have the form of hooks and loops (such as touch-and-close fasteners), e.g. fasteners retailed under the designation "VELCRO". An example of one such garment is described in WO-Al-94/26224.

It is also well known within this particular field to use loose belts to which an absorbent unit is fastened, therewith enabling one and the same belt to be used over a longer period of time and together with a number of changes of absorbent units. A loose belt of this kind is intended for use with an absorbent unit illustrated and described in WO-Al-94/26225.

TECHNICAL PROBLEMS

One well known problem with belted garments of the aforesaid kind exists in the handling of those parts of the belt that protrude out from each side of the absorbent part of the combined garment, so as to enable the belt-portions to be gripped quickly and correctly and then fastened together. With respect in particular to incontinence problems, it will be understood that persons suffering from incontinence are often old and physically handicapped in some way or another. Consequently, there is need of a solution which will enable the absorbent garment to be correctly positioned on the wearer in a simple fashion.

A solution to this problem is taught by WO-Al-94/26222, according to which the belt is given a degree of stiffness such as to prevent excessive wrinkling of the belt and therewith facilitate handling of said belt.

Another aspect of the use of a stiff or rigid belt is described in UK Patent Specification GB-A-2,216,774, where a portion of the waist part, which can be interpreted as a belt-portion, comprises a stiffening element. It is said that this stiffening element functions to reduce wrinkling in this region, therewith reducing the risk of leakage.

U.S. Pat. No. 3,587,580 discloses a garment comprising an absorbent part and a waist belt which has a longitudinal direction and a cross-direction and which is attached directly or indirectly to said garment, wherein said belt includes two belt portions which extend generally in said longitudinal direction in respective directions from said absorbent part and which are intended to be fastened together around a wearer of the garment, wherein the belt has a stiffness that varies in the cross-direction of the belt.

It is thus desirable from several aspects to use a belt which has a relatively high stiffness. Unfortunately, however, a very stiff belt is liable to cause discomfort to the wearer in use, for instance is liable to cut into and chafe the wearer's skin. In addition, a stiff belt has relatively little pliability and will not therefore adapt readily to the shape of the wearer's body. This problem is particularly significant in the case of broad belts, which are consequently often felt particularly uncomfortable to wear.

There is thus also a need of a solution which will allow the use of a relatively stiff, or rigid, belt, that is comfortable to wear and that will not increase the danger of the belt cutting into and chafing the wearer's skin.

SUMMARY OF THE INVENTION

The aforesaid problems are avoided essentially completely with the present invention. Thus, an object of the present invention is to provide a belt with which the risk of chafing the wearer's skin and causing other forms of skin irritation is markedly reduced. An inventive belt is primarily characterised in that it has a stiffness which varies in the cross-direction of the belt.

By configuring the belt with a stiffness which is greater in a longitudinally extending central part of the belt than in at least one longitudinally extending edge-part of said belt, there is provided a belt whose stiffness is sufficient to avoid the aforesaid handling and leakage problems while, at the same time, providing a soft belt edge which is comfortable to the user. Because the edge of the belt has a low degree of stiffness, it can be adapted to the shape of the wearer's body without impairing wearer comfort. A belt comprising an essentially homogeneous material is given the desired properties, for instance, by making the cross-sectional area smaller at the edge-parts of the belt than at the central part thereof. A belt of this design is particularly beneficial when the cross-sectional area decreases continuously from the longitudinally extending centre line of the belt towards the longitudinal edges of said belt.

Other preferred characteristic features of the invention and further embodiments thereof will be apparent from the following dependent claims.

BRIEF DESCRIPTION OF THE DRAWINGS

The present invention will now be described in more detail with reference to the accompanying drawings, in which.

DETAILED DESCRIPTION OF PREFERRED EMBODIMENTS

Figure 1:
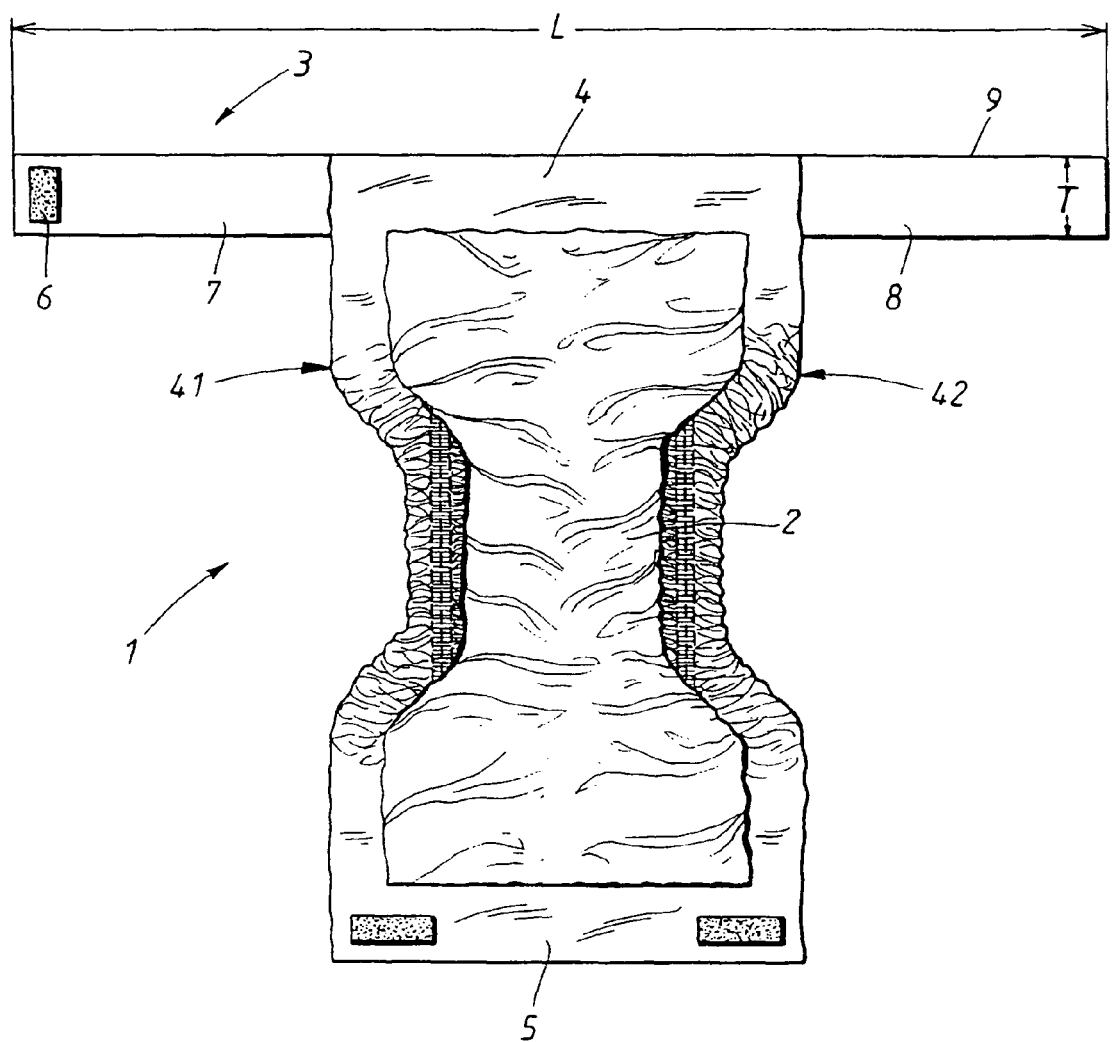
FIG. 1 illustrates a garment which comprises a belt constructed in accordance with the invention.

FIG. 1 shows a garment generally referenced 1. The garment comprises an absorbent part 2 and a belt-portion, generally referenced 3. The belt may be a full belt 3 which is fastened to the absorbent part at its one end 4 (or 5). Alternatively, the belt 3 may comprise two mutually separate parts disposed on respective sides of the absorbent part 2 at one end 4 of said absorbent part. The illustrated belt has a longitudinal direction L and a cross-direction T. The manner in which the belt is fastened is not significant to the present field of use. Thus, the belt 3 may be fastened permanently to the absorbent part 2, i.e. glued, welded, sewn thereto or fastened thereto in some other way. Releasable fastener devices may also be used, such as buttons, press-studs, clips, touch-and-close fasteners, or corresponding means.

If it is desired to incorporate suppleness and resilience in a belt that includes two mutually separate parts, it is conceivable for one end 4 (or 5) of the absorbent part of the garment to be made elastic.

The general appearance of the illustrated garment is known to the art and consequently not all of the component parts of said garment will be described in detail in this document. The belt 3 comprises a first belt-portion 7 that projects out from one first side-edge 41 of the absorbent part 2, and a second belt-portion 8 that projects out from the opposing side-edge 42 of said absorbent part. A fastener device 6 in the form of a surface that presents hooked elements and forming part of a touch-and-close fastener means is provided on one end portion of the first belt-portion 7. The fastener device 6 may either be fastened to the other belt-portion 8 (on the side thereof not shown in FIG. 1) or to a receiving area that includes loop-elements and arranged on the second belt-portion 8. The fastener device 6 may alternatively consist of an adhesive material which is either fastened to the second belt-portion 8 (on the side thereof not shown in FIG. 1) or to a specially designed receiving surface against which the adhesive fastener device 6 can be fastened and released repeatedly.

As is made apparent hereinafter, further advantages are afforded by special dimensions and designs of the belt 3. Although the belt is preferably generally oblong in shape, it may, of course, have other elongated shapes. However, when the belt has an oblong shape its width will preferably lie between 70 mm and 160 mm so as to enable the belt to be used by adults that are incontinent.

When using an inventive belt, the belt-portions 7 and 8 can be given good handling properties by choosing a belt material that is sufficiently stiff to avoid wrinkling problems while, nevertheless, avoiding problems associated with reduced wearer comfort, such as chafing of and biting into the wearer's skin.

A nonwoven material is preferably used for either one side or both sides of the belt, said nonwoven material preferably being of the kind to which hooked elements on the fastener device 6 can be releasably fastened. The use of nonwoven material as a receiving surface to which the fastener device 6 can be releasably fastened enables particularly beneficial combinations of peeling forces and shear strengths to be obtained. The use of nonwoven material is also beneficial by virtue of the fact that it is less expensive than woven material and thus more appropriate for use with disposable garments.

Since wearer comfort is a particularly important factor to which attention must be paid within this field, and then particularly with regard to belt stiffness, it has been found advantageous to construct the belt in accordance with the present invention. As before mentioned, the belt will beneficially have a certain degree of stiffness, particularly in its longitudinal direction L. At the same time, the risk of the belt edges cutting into the wearer's skin or chafing the wearer's skin is greater in the case of a stiff belt than in the case of a belt which is softer and more pliable. With the intention of addressing this risk, the inventive belt is constructed so that its stiffness will vary in the cross-direction T of the belt, thereby enabling the belt to conform to the shape of the wearer's body in use much more readily than might otherwise be the case.

Figure 2:
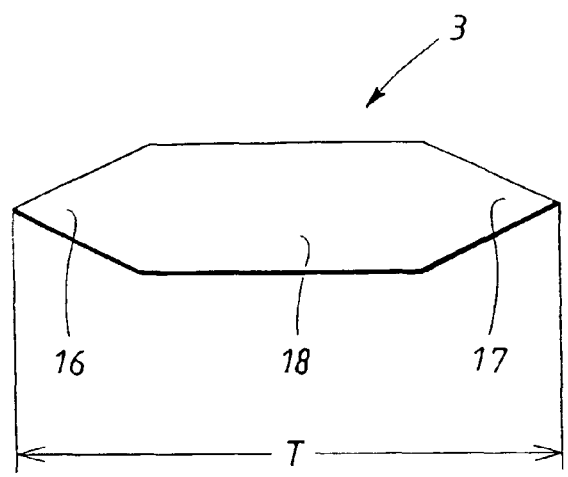
FIG. 2 is a cross-sectional view of the belt shown in FIG. 1.

FIG. 2 is a cross-sectional view of the belt 3 shown in FIG. 1. As will be apparent, the belt, which has a generally homogeneous construction, comprises a central part 18 that is of predetermined stiffness. Because the belt has been constructed so that the cross-sectional area of said belt decreases in a direction towards the edge-parts 16 and 17 thereof, the stiffness of the belt will also decrease continuously in said edge-parts 16, 17. These parts 16 and 17 can thus conform to the wearer in use, for instance bulge out when necessary, therewith reducing the risk of chafing and of the belt cutting into the wearer's skin and also reducing the risk of impaired user comfort.

Figure 3:
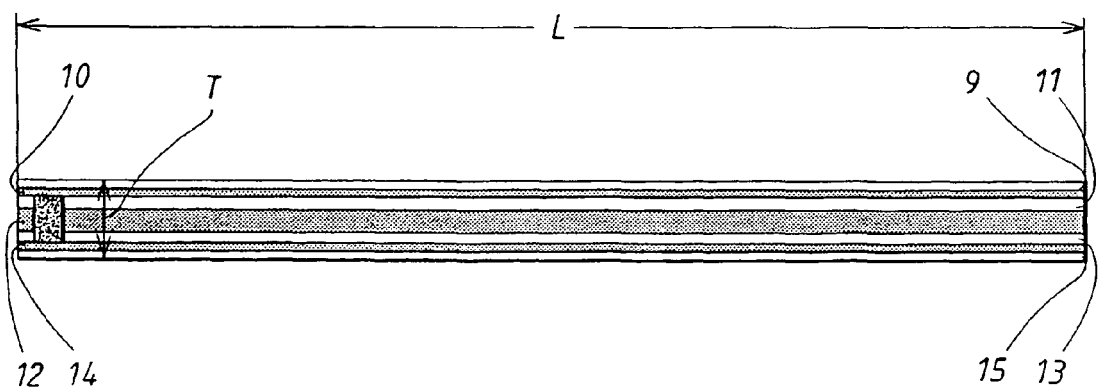
FIG. 3 illustrates another embodiment of an inventive belt.

FIG. 3 illustrates another embodiment of the present invention in which the belt 3 comprises in its cross-direction T a plurality of mutually adjacent regions 9, 10, 11, 12, 13, 14 and 15 of mutually different stiffness, the extensions of these regions in the longitudinal direction L coinciding essentially with the length of the belt 3. These regions are preferably disposed so that the central part of the belt will be stiffer than the edge-parts of said belt. It is also conceivable for the belt to be constructed so that only one edge-part will have this greater pliability, preferably that edge-part which lies uppermost in use. Neither is it necessary for the regions 9, 10, 11, 12, 13, 14 and 15 to extend through the full thickness of the belt. For instance, these regions may be disposed on a layer 20 that is preferably placed proximal to the wearer's body in use.

Figure 4:
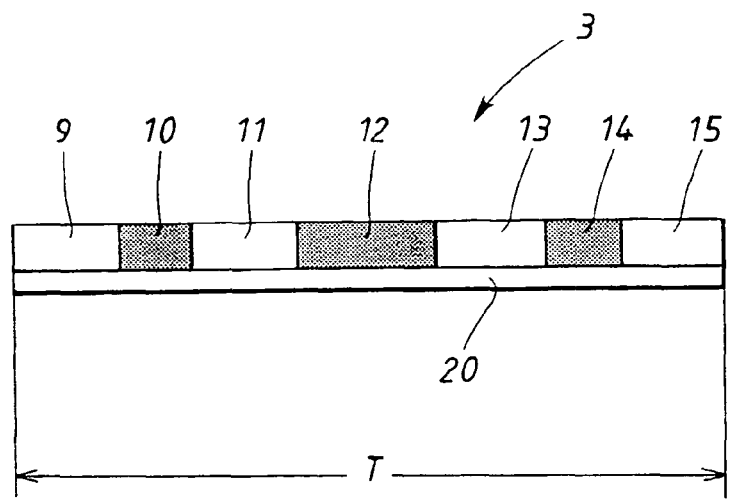
FIG. 4 is a cross-sectional view of the belt shown in FIG. 3.

FIG. 4 is a cross-sectional view of the belt 3 shown in FIG. 3 provided with a layer 20 which by virtue of its holding effect on said regions 9-15 facilitates manufacture of the belt, in addition to enhancing wearer comfort.

Figure 5:
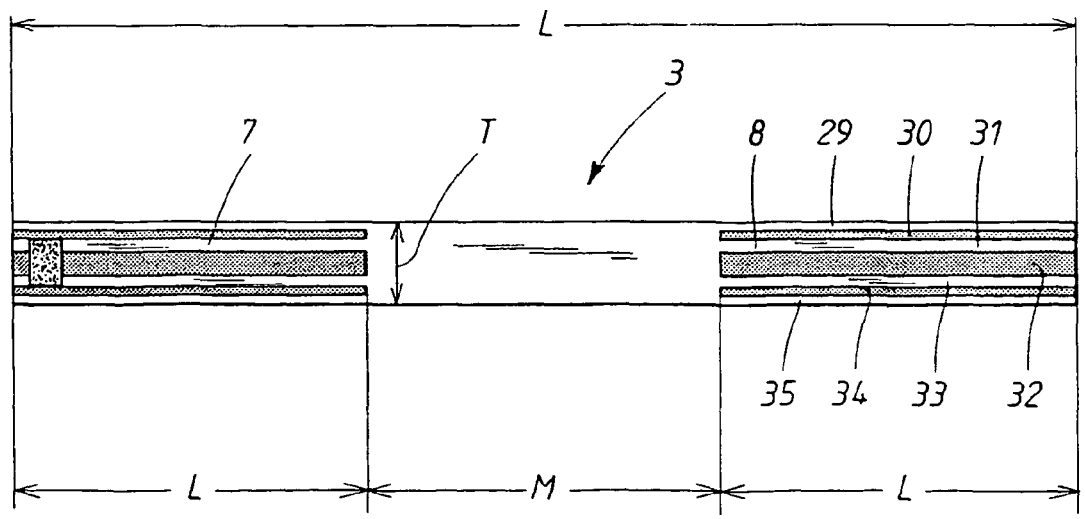
FIG. 5 illustrates a third embodiment of an inventive belt.

FIG. 5 illustrates a third embodiment of a continuous belt constructed in accordance with the present invention. The belt 3 of the FIG. 5 embodiment includes a plurality of mutually adjacent regions 29, 30, 31, 32, 33, 34, 35 of mutually different stiffness in the cross-direction T of the belt, said regions being disposed on a first and a second belt-portion 7, 8. A part M of the belt 3 located centrally between the two stiffened belt-portions 7, 8 as seen in the longitudinal direction of the belt 3 includes no stiffening material and thus has one and the same degree of stiffness throughout the whole of its area. Thus, those portions 7, 8 of the belt that include regions of mutually different stiffness have an extension in the longitudinal direction L which is shorter than the length of the belt 3. In this case, said regions are placed so as to essentially coincide with the wearer's need for soft edge-parts on the belt 3.

In certain applications, it may be sufficient for the belt to have two longitudinally extending regions of mutually different stiffness. Furthermore, it may be appropriate to leave a piece of each end of the belt free from stiffening material, for instance when the belt is fastened together with the aid of a button/buttonhole fastener. This would facilitate buttoning of the belt. It is therefore not necessary for the belt to have regions of different stiffness along the whole of its length.

One method of achieving the desired difference in stiffness between different parts of the belt in its cross-direction is to treat the edge-parts of the belt in a manner to change the internal structure of the material. According to one embodiment of the invention (not shown), the edge-parts of the belt are softened by heat-treating said parts. According to another embodiment (also not shown) edge-parts of the belt are softened by exposing said edges to radiation, whereas said softening effect is achieved in accordance with another embodiment (not shown) by mechanically working said edge-parts.

Naturally, combinations of the aforesaid methods can be used to produce the desired material properties within the scope of the invention.

The invention shall not therefore be considered limited to the aforedescribed exemplifying embodiments thereof, since other embodiments are conceivable within the scope of the following Claims.

The invention claimed is:

1. A garment comprising an absorbent part and a waist belt which has a longitudinal direction and a cross-direction and which is attached directly or indirectly to said garment, wherein said belt includes two belt-portions which extend generally in said longitudinal direction in respective directions from said absorbent part and which are intended to be fastened together around a wearer of the garment, which belt has a stiffness that varies in the cross-direction of the belt, wherein the stiffness that varies has an extension in the longitudinal direction that essentially coincides with the length of the belt, wherein a part of the belt being located centrally between the two belt-portions has one and the same degree of stiffness throughout the whole of its area.

2. A garment comprising an absorbent part and a waist belt which has a longitudinal direction and a cross-direction and which is attached directly or indirectly to said garment, wherein said belt includes two belt-portions which extend generally in said longitudinal direction in respective directions from said absorbent part and which are intended to be fastened together around a wearer of the garment, which belt has a stiffness that varies in the cross-direction of the belt, wherein the stiffness that varies has an extension in the longitudinal direction that essentially coincides with the length of the belt, wherein the two belt-portions of said belt are comprised of a generally homogeneous material; and a cross-section through one or both of said belt-portions taken in the cross-direction presents at least one longitudinally extending edge-part that is thinner than a central part of said cross-section.

3. A garment comprising an absorbent part and a waist belt which has a longitudinal direction and a cross-direction and which is attached directly or indirectly to said garment, wherein said belt includes two belt-portions which extend generally in said longitudinal direction in respective directions from said absorbent part and which are intended to be fastened together around a wearer of the garment, which belt has a stiffness that varies in the cross-direction of the belt, wherein the stiffness that varies has an extension in the longitudinal direction that essentially coincides with the length of the belt, wherein at least one longitudinally extending edge-part of the belt has been treated so as to change the stiffness of the material locally.

4. A garment according to claim 3, wherein the at least one edge-part of said belt has been heat-treated.

5. A garment according to claim 3, wherein the at least one edge-part of said belt has been treated with electromagnetic radiation.

6. A garment according to claim 3, wherein the at least one edge-part of said belt has been worked mechanically.

7. A garment comprising an absorbent part and two separate belts which have a longitudinal direction, a cross-direction, longitudinally extending edge parts and a longitudinally extending interior part that is arranged between the longitudinally extending edge parts, wherein said belts extend generally in said longitudinal direction, one end of each of the two separate belts is permanently fastened directly or indirectly to the absorbent part, and opposite ends of each of the two separate belts extend in respective directions from said absorbent part and are adapted to be fastened together around a wearer of the garment, which belts have a stiffness that varies in the cross-direction of the belts, wherein the stiffness that varies has an extension in the longitudinal direction, and wherein a thickness of each of the cross-sectional areas at the longitudinally extending edge-parts of the belts is smaller than at the longitudinally extending interior part thereof.

8. The garment of claim 7, wherein the stiffness that varies has an extension that essentially coincides with the length of the belts.

9. The garment of claim 7, wherein the belts fasten with releasable fasteners.

10. The garment of claim 7, wherein one end of the absorbent part is elastic.

11. The garment of claim 7, wherein the thickness of the interior part is substantially uniform.

12. The garment of claim 11, wherein a width of the interior part is greater than a width of each of the longitudinally extending edge parts.

13. A garment comprising an absorbent part and two separate belts which have a longitudinal direction, a cross-direction, longitudinally extending edge parts and a longitudinally extending interior part that is arranged between the longitudinally extending edge parts, wherein said belts extend generally in said longitudinal direction, one end of each of the two separate belts is permanently fastened directly or indirectly to the absorbent part, and opposite ends of each of the two separate belts extend in respective directions from said absorbent part and are adapted to be fastened together around a wearer of the garment, which belts have a stiffness that varies in the cross-direction of the belts, wherein the stiffness that varies has an extension in the longitudinal direction, and wherein the stiffness at the edge-parts of the belts is less than at the interior part thereof.

14. The garment of claim 13, wherein the stiffness that varies has an extension that essentially coincides with the length of the belts.

15. The garment of claim 13, wherein the belts fasten with releasable fasteners.

16. The garment of claim 13, wherein one end of the absorbent part is elastic.

17. The garment of claim 13, wherein a width of the interior part is greater than a width of each of the longitudinally extending edge parts.

18. A garment comprising an absorbent part and two separate waist belts which have a longitudinal direction, a cross-direction, longitudinally extending edge parts and a longitudinally extending interior part that is arranged between the longitudinally extending edge parts,
wherein said belts extend generally in said longitudinal direction, one end of each of the two separate belts is permanently fastened directly or indirectly to the absorbent part, and opposite ends of each of the two separate belts extend in respective directions from said absorbent part and are adapted to be fastened together around a wearer of the garment, which belts having a stiffening material that forms a stiffness that varies in the cross-direction of the belts,
wherein the stiffness that varies has an extension in the longitudinal direction, and
wherein the interior part of the belts in a cross section taken in the cross-direction has a substantially uniform thickness, the substantially uniform thickness continuously decreasing from the interior part to each of the edge parts in the cross section and the stiffness of the belts continuously decreasing from the interior part to each of the edge parts in the cross section.

19. The garment of claim 18, wherein the stiffness that varies has an extension that essentially coincides with the length of the belts.

20. The garment of claim 18, wherein the belts fasten with releasable fasteners.

21. The garment of claim 18, wherein one end of the absorbent part is elastic.

22. The garment of claim 18, wherein a piece at an end of both of the belts is free from stiffening material.

23. The garment of claim 18, wherein a piece at an end of at least one of the belts is free from stiffening material.

24. The garment according to claim 18, wherein the cross section of the belts has substantially homogeneous construction of the stiffening material.

25. The garment according to claim 18, wherein the interior part has a substantially uniform stiffness in the cross section.

26. A garment comprising an absorbent part and two separate belts which have a longitudinal direction, a cross-direction, longitudinally extending edge parts and a longitudinally extending interior part that is arranged between the longitudinally extending edge parts, wherein said belts extend generally in said longitudinal direction, one end of each of the two separate belts is permanently fastened directly or indirectly to the absorbent part, and opposite ends of each of the two separate belts extend in respective directions from said absorbent part and are adapted to be fastened together around a wearer of the garment, which belts have a stiffness that varies in the cross-direction of the belts, wherein the stiffness that varies has an extension in the longitudinal direction, and wherein the longitudinally extending edge parts are adjacent the central part, the stiffness at the edge-parts of the belts is less than at the interior part thereof, and the stiffness of the interior part is substantially uniform along a cross-direction.

27. The garment of claim 26, wherein the stiffness that varies has an extension that essentially coincides with the length of the belts.

28. The garment of claim 26, wherein the belts fasten with releasable fasteners.

29. The garment of claim 26, wherein one end of the absorbent part is elastic.

30. The garment of claim 26, the stiffness of the interior part is substantially uniform along the longitudinal direction.

* * * * *